(12) United States Patent
Cardinali et al.

(10) Patent No.: US 11,147,931 B2
(45) Date of Patent: Oct. 19, 2021

(54) DRUG DELIVERY DEVICE WITH AIR AND BACKFLOW ELIMINATION

(71) Applicant: Insulet Corporation, Acton, MA (US)

(72) Inventors: Steven Cardinali, Woburn, MA (US); David Nazzaro, Groveland, MA (US); Lawrence S. Ring, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 371 days.

(21) Appl. No.: 16/191,891

(22) Filed: Nov. 15, 2018

(65) Prior Publication Data
US 2019/0151568 A1    May 23, 2019

Related U.S. Application Data

(60) Provisional application No. 62/587,812, filed on Nov. 17, 2017.

(51) Int. Cl.
*A61M 5/36* (2006.01)
*A61K 38/28* (2006.01)
(Continued)

(52) U.S. Cl.
CPC ............... *A61M 5/36* (2013.01); *A61K 38/28* (2013.01); *A61M 5/14248* (2013.01); *A61M 5/158* (2013.01); *A61M 5/16813* (2013.01); *A61M 5/16886* (2013.01); *A61M 2005/1402* (2013.01); *A61M 2005/1406* (2013.01)

(58) Field of Classification Search
CPC .............. A61M 5/14248; A61M 5/158; A61M 5/14276; A61M 37/0015; A61M 5/14244; A61M 5/2448; A61M 5/36; A61K 38/28
See application file for complete search history.

(56) References Cited

U.S. PATENT DOCUMENTS 303,013 A     8/1884  Horton
306,691 A    10/1884  Johnson
(Continued)

FOREIGN PATENT DOCUMENTS

DE      19723648 C1    8/1998
DE      19920896 A1   11/2000
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Kacvinsky Daisak Bluni PLLC

(57) ABSTRACT

A wearable drug delivery device that can deliver a liquid drug stored in a container to a patient or user is provided. A soft needle or cannula can be placed in fluid communication with the liquid drug and can be coupled to a needle insertion component that provides access to the patient. A drive system of the drug delivery device can expel the liquid drug from the container to the patient through the soft needle or cannula. The wearable drug delivery device can include components for preventing backflow and eliminating air within the liquid drug. As a result, the comfort of the patient can be enhanced and correct drug dosages can be provided when using the drug delivery device.

20 Claims, 6 Drawing Sheets

(51) Int. Cl.
  *A61M 5/142*  (2006.01)
  *A61M 5/168*  (2006.01)
  *A61M 5/158*  (2006.01)
  *A61M 5/14*   (2006.01)

(56) References Cited

U.S. PATENT DOCUMENTS

| | | |
|---|---|---|
| 315,727 A | 4/1885 | Church |
| 405,524 A | 6/1889 | Benton |
| 410,817 A | 9/1889 | Weeks, Jr. |
| 2,667,986 A | 2/1954 | Perelson |
| 3,631,847 A | 1/1972 | Hobbs |
| 3,792,703 A | 2/1974 | Moorehead |
| 3,812,843 A | 5/1974 | Wootten |
| 3,841,328 A | 10/1974 | Jensen |
| 3,885,662 A | 5/1975 | Schaefer |
| 4,067,000 A | 1/1978 | Carlson |
| 4,151,845 A | 5/1979 | Clemens |
| 4,152,098 A | 5/1979 | Moody et al. |
| 4,193,397 A | 3/1980 | Tucker et al. |
| 4,211,998 A | 7/1980 | Junginger et al. |
| 4,231,019 A | 10/1980 | Junginger et al. |
| 4,261,388 A * | 4/1981 | Shelton ............ A61M 5/1689 137/486 |
| 4,268,150 A | 5/1981 | Chen |
| 4,276,170 A * | 6/1981 | Vaillancourt ......... B01D 35/00 210/436 |
| 4,342,311 A | 8/1982 | Whitney et al. |
| 4,346,385 A | 8/1982 | Schiavone et al. |
| 4,364,385 A | 12/1982 | Lossef |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 4,985,016 A * | 1/1991 | Theeuwes ............ A61M 5/1407 604/85 |
| 4,994,047 A | 2/1991 | Walker |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,261,884 A | 11/1993 | Stern et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Bocker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,678,539 A | 10/1997 | Schubert et al. |
| 5,685,859 A | 11/1997 | Kornerup |
| 5,693,018 A | 12/1997 | Kriesel et al. |
| 5,695,490 A | 12/1997 | Flaherty et al. |
| 5,702,363 A | 12/1997 | Flaherty |
| 5,704,520 A | 1/1998 | Gross |
| 5,716,343 A | 2/1998 | Kriesel et al. |
| 5,726,404 A | 3/1998 | Brody |
| 5,726,751 A | 3/1998 | Altendort et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,810,015 A | 9/1998 | Flaherty |
| 5,814,020 A | 9/1998 | Gross |
| 5,840,063 A | 11/1998 | Flaherty |
| 5,845,218 A | 12/1998 | Altschul |
| 5,848,990 A | 12/1998 | Cirelli et al. |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley et al. |
| 5,865,806 A | 2/1999 | Howell |
| 5,871,470 A | 2/1999 | McWha |
| 5,875,393 A | 2/1999 | Altschul et al. |
| 5,878,539 A | 3/1999 | Grubb |
| 5,885,808 A | 3/1999 | Spooner et al. |
| 5,886,647 A | 3/1999 | Badger et al. |

(56) References Cited

U.S. PATENT DOCUMENTS

| | | |
|---|---|---|
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,921,419 A | 7/1999 | Niedospial, Jr. et al. |
| 5,931,814 A | 8/1999 | Alex et al. |
| 5,935,099 A | 8/1999 | Peterson et al. |
| 5,954,058 A | 9/1999 | Flaherty |
| 5,954,694 A | 9/1999 | Sunseri |
| 5,957,890 A | 9/1999 | Mann et al. |
| 5,957,895 A | 9/1999 | Sage et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,050,978 A | 4/2000 | Orr et al. |
| 6,071,292 A | 6/2000 | Makower et al. |
| 6,090,092 A | 7/2000 | Fowles et al. |
| 6,126,637 A | 10/2000 | Kriesel et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,200,338 B1 | 3/2001 | Solomon et al. |
| 6,206,850 B1 | 3/2001 | ONeil |
| 6,244,776 B1 | 6/2001 | Wiley |
| 6,244,778 B1 | 6/2001 | Chesbrough |
| 6,309,370 B1 | 10/2001 | Ben-Haim et al. |
| 6,363,609 B1 | 4/2002 | Pickren |
| 6,375,639 B1 | 4/2002 | Duplessie et al. |
| 6,475,196 B1 | 11/2002 | Vachon |
| 6,520,936 B1 | 2/2003 | Mann |
| 6,527,744 B1 | 3/2003 | Kriesel et al. |
| 6,569,125 B2 | 5/2003 | Jepson et al. |
| 6,572,542 B1 | 6/2003 | Houben et al. |
| 6,572,585 B2 | 6/2003 | Choi |
| 6,666,852 B2 | 12/2003 | Niedospial, Jr. |
| 6,699,221 B2 | 3/2004 | Vaillancourt |
| 6,740,059 B2 | 5/2004 | Flaherty |
| 6,883,778 B1 | 4/2005 | Newton et al. |
| 7,008,404 B2 | 3/2006 | Nakajima |
| 7,018,360 B2 | 3/2006 | Flaherty et al. |
| 7,025,744 B2 | 4/2006 | Utterberg et al. |
| 7,060,059 B2 * | 6/2006 | Keith .............. G16H 20/17 604/504 |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,267,665 B2 * | 9/2007 | Steil .............. A61B 5/14532 604/131 |
| 7,291,133 B1 | 11/2007 | Kindler et al. |
| 7,303,549 B2 | 12/2007 | Flaherty et al. |
| 7,918,825 B2 | 4/2011 | O'Connor et al. |
| 9,402,950 B2 | 8/2016 | Diianni et al. |
| 2001/0053895 A1 | 12/2001 | Vaillancourt |
| 2002/0010423 A1 | 1/2002 | Gross et al. |
| 2002/0032374 A1 | 3/2002 | Holker et al. |
| 2002/0066715 A1 | 6/2002 | Niedospial |
| 2002/0123740 A1 | 9/2002 | Flaherty et al. |
| 2003/0163097 A1 | 8/2003 | Fleury et al. |
| 2004/0010207 A1 | 1/2004 | Flaherty et al. |
| 2004/0064088 A1 | 4/2004 | Gorman et al. |
| 2004/0088224 A1 | 5/2004 | Mukai |
| 2004/0092865 A1 | 5/2004 | Flaherty et al. |
| 2004/0116847 A1 | 6/2004 | Wall |
| 2004/0158208 A1 * | 8/2004 | Hiejima .............. A61M 39/26 604/167.04 |
| 2004/0203357 A1 | 10/2004 | Nassimi |
| 2005/0020980 A1 | 1/2005 | Inoue et al. |
| 2005/0187524 A1 | 8/2005 | Willis et al. |
| 2005/0203461 A1 | 9/2005 | Flaherty et al. |
| 2005/0238507 A1 | 10/2005 | Dilanni et al. |
| 2005/0258581 A1 | 11/2005 | Tanaka |
| 2006/0134323 A1 | 6/2006 | O'Brien |
| 2006/0155210 A1 | 7/2006 | Beckman et al. |
| 2006/0178633 A1 | 8/2006 | Garibotto et al. |
| 2006/0204535 A1 | 9/2006 | Johnson |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0025811 A1 | 2/2007 | Wilhelm |
| 2007/0112332 A1 | 5/2007 | Harding et al. |
| 2007/0118405 A1 | 5/2007 | Campbell et al. |
| 2007/0129690 A1 | 6/2007 | Rosenblatt et al. |
| 2007/0173974 A1 | 7/2007 | Lin |
| 2007/0197163 A1 | 8/2007 | Robertson |
| 2007/0282269 A1 | 12/2007 | Carter et al. |
| 2008/0004515 A1 | 1/2008 | Jennewine |
| 2008/0006500 A1 | 1/2008 | Spahr |
| 2008/0051738 A1 | 2/2008 | Griffin |
| 2008/0065050 A1 | 3/2008 | Sparks et al. |
| 2008/0078400 A1 | 4/2008 | Martens et al. |
| 2008/0132880 A1 | 6/2008 | Buchman |
| 2008/0249508 A1 | 10/2008 | Lopez et al. |
| 2008/0287906 A1 | 11/2008 | Burkholz et al. |
| 2009/0054866 A1 | 2/2009 | Teisen-Simony et al. |
| 2009/0062767 A1 | 3/2009 | Van Antwerp et al. |
| 2009/0069787 A1 | 3/2009 | Estes et al. |
| 2009/0099521 A1 | 4/2009 | Gravesen et al. |
| 2009/0124979 A1 | 5/2009 | Raymond et al. |
| 2009/0198215 A1 | 8/2009 | Chong et al. |
| 2009/0299300 A1 | 12/2009 | Truitt et al. |
| 2010/0137784 A1 | 6/2010 | Cefai et al. |
| 2010/0152658 A1 | 6/2010 | Hanson et al. |
| 2011/0054390 A1 | 3/2011 | Searle et al. |
| 2011/0054399 A1 | 3/2011 | Chong et al. |
| 2011/0144586 A1 | 6/2011 | Michaud et al. |
| 2011/0166512 A1 | 7/2011 | Both et al. |
| 2011/0230833 A1 | 9/2011 | Landman et al. |
| 2011/0251509 A1 | 10/2011 | Beyhan et al. |
| 2011/0316562 A1 | 12/2011 | Cefai et al. |
| 2012/0003093 A1 | 1/2012 | Lischer et al. |
| 2012/0003935 A1 | 1/2012 | Lydon et al. |
| 2012/0010594 A1 | 1/2012 | Holt et al. |
| 2012/0078161 A1 | 3/2012 | Masterson et al. |
| 2012/0238851 A1 | 9/2012 | Kamen et al. |
| 2012/0277668 A1 | 11/2012 | Chawla |
| 2013/0060233 A1 | 3/2013 | O'Connor et al. |
| 2013/0178791 A1 | 7/2013 | Javitt |
| 2013/0317753 A1 | 11/2013 | Kamen et al. |
| 2014/0074033 A1 | 3/2014 | Sonderegger et al. |
| 2014/0127048 A1 | 5/2014 | Diianni et al. |
| 2014/0128839 A1 | 5/2014 | Dilanni et al. |
| 2014/0135880 A1 | 5/2014 | Bumgartner et al. |
| 2014/0316379 A1 | 10/2014 | Sonderegger et al. |
| 2016/0015891 A1 | 1/2016 | Papiorek |
| 2016/0038689 A1 | 2/2016 | Lee et al. |
| 2016/0302054 A1 | 10/2016 | Kimura et al. |
| 2017/0128664 A1 | 5/2017 | Diianni et al. |

FOREIGN PATENT DOCUMENTS

| | | |
|---|---|---|
| EP | 0341049 A2 | 11/1989 |
| EP | 0496305 A2 | 7/1992 |
| EP | 0763369 A1 | 3/1997 |
| EP | 0867196 A2 | 9/1998 |
| EP | 0937475 A2 | 8/1999 |
| EP | 2397181 A1 | 12/2011 |
| EP | 2830499 A1 | 2/2015 |
| GB | 875034 A | 8/1961 |
| GB | 2443261 A | 4/2008 |
| TW | 200740148 A | 10/2007 |
| TW | M452390 U | 5/2013 |
| WO | 8101658 A1 | 6/1981 |
| WO | 8606796 A1 | 11/1986 |
| WO | 9800193 A1 | 1/1998 |
| WO | 9801071 A1 | 1/1998 |
| WO | 9856293 A1 | 12/1998 |
| WO | 9910040 A1 | 3/1999 |
| WO | 9956803 A1 | 11/1999 |

(56) References Cited

FOREIGN PATENT DOCUMENTS

| | | | |
|---|---|---|---|
| WO | 9962576 | A1 | 12/1999 |
| WO | 0019887 | A1 | 4/2000 |
| WO | 0029047 | A1 | 5/2000 |
| WO | 0029049 | A1 | 5/2000 |
| WO | 0030705 | A1 | 6/2000 |
| WO | 0061215 | A1 | 10/2000 |
| WO | 0074752 | A1 | 12/2000 |
| WO | 0078210 | A1 | 12/2000 |
| WO | 0152727 | A1 | 7/2001 |
| WO | 0156633 | A2 | 8/2001 |
| WO | 0172354 | A2 | 10/2001 |
| WO | 0176684 | A1 | 10/2001 |
| WO | 2002015954 | A1 | 2/2002 |
| WO | 0220073 | A2 | 3/2002 |
| WO | 0226282 | A2 | 4/2002 |
| WO | 0240083 | A2 | 5/2002 |
| WO | 2002068823 | A1 | 9/2002 |
| WO | 03090509 | A2 | 11/2003 |
| WO | 2006053007 | A2 | 5/2006 |
| WO | 2007064835 | A2 | 6/2007 |
| WO | 2008024810 | A2 | 2/2008 |
| WO | 2008133702 | A1 | 11/2008 |
| WO | 2009098648 | A2 | 8/2009 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012134589 | A1 | 10/2012 |
| WO | 2013078200 | A1 | 5/2013 |
| WO | 2013134486 | A2 | 9/2013 |
| WO | 2013149186 | A1 | 10/2013 |
| WO | 2013182321 | A1 | 12/2013 |
| WO | 2014194183 | A2 | 12/2014 |
| WO | 2015061493 | A1 | 4/2015 |
| WO | 2015081337 | A2 | 6/2015 |
| WO | 2016141082 | A1 | 9/2016 |
| WO | 2017205816 | A1 | 11/2017 |

OTHER PUBLICATIONS

International Search Report and Written Opinion for Application No. PCT/US2017/015601, dated May 16, 2017, 6 pages.

International Search Report and Written Opinion for Application No. PCT/US18/52464, dated Jan. 4, 2019, 14 pages.

International Search Report and Written Opinion for Application No. PCT/US18/18901, dated Aug. 6, 2018, 15 pages.

International Preliminary Report on Patentability for the International Patent Application No. PCT/US2018/018901, dated Sep. 6, 2019, 8 pages.

International Preliminary Report on Patentability dated Oct. 9, 2014, issued in PCT Patent Application No. PCT/US2013/034674, 15 pages.

EPO Search Report dated Nov. 11, 2015, received in corresponding Application No. 13768938.6, 7 pgs.

European Patent Office, "Notification of Transmittal of the ISR and the Written Opinion of the International Searching Authority, or the Declaration," in PCT Application No. PCT/GB2015/050248, dated Jun. 23, 2015, 12 pages.

U.K. Intellectual Property Office, GB Application No. GB 1401591. 1, ""Search Report underSection 17(5)"" dated Jul. 9, 2015, 3 pages.

International Preliminary Report on Patentability dated Apr. 9, 2020, issued in PCT Patent Application No. PCT/US2018/052464, 7 pages.

International Search Report for the International Patent Application No. PCT/US03/16640, dated Oct. 3, 2003, 1 page.

User's Guide for Model 508 Insulin Pump, Mini Med, 8/00, 145 pages.

Web-Site Brochure dated Jan. 4, 2000. SOOIL—Homepage. "Portable Insulin Pump". www.sooil.com/product2.htm.

Web-Site Brochure dated Jan. 4, 2000. SOOIL—Homepage. ""Portable Insulin Pump"".www.sooil.com/product3.htm.

Web-Site Brochure dated Jan. 4, 2000. SOOIL—Homepage. "Portable Insulin Pump". www.sooil.com/product4.htm.

Web-Site Brochure dated Dec. 20, 1999. "The Animas R-1000 Insulin Pump". www .animascorp.com/pump f _ s.html.

Web-Site Brochure dated Dec. 20, 1999. ""The Animas R-1000 Insulin Pump"" www.animascorp.com/pump_f_f.html.

Web-Site Brochure dated Jan. 4, 2000. SOOIL—Homepage. ""Ponable Insulin Pump"".www.sooil.com/intro2.htm.

Web-Site Brochure dated Jan. 4, 2000. MiniMed 508. "Doing its job. Naturally." www.minimed.com/tiles/mm 113.htm.

Web-Site Brochure dated Dec. 20, 1999. Applied Medical Technology. •""508 Pump Information"". www.applied-medical.co.uk/508.htm.

Web-Site Brochure dated Jan. 4, 2000. ""The Glucose Sensor"". www.animascorp.com/sensor f.html.

\* cited by examiner

DRUG DELIVERY DEVICE WITH AIR AND BACKFLOW ELIMINATION

CROSS REFERENCE TO RELATED APPLICATIONS

This application claims the benefit of U.S. Provisional Application No. 62/587,812, filed Nov. 17, 2017, which is incorporated herein by reference in its entirety.

TECHNICAL FIELD

Embodiments generally relate to medication delivery. More particularly, embodiments relate to providing flow of a liquid drug from a drug delivery device in a manner that eliminates air entrainment and backflow.

BACKGROUND

Many conventional drug delivery systems, such as handheld auto-injectors, are designed to rapidly deliver a drug to a patient. These conventional drug delivery systems are generally not suitable for delivering a drug to a user over relatively longer periods of time as may be required for many drugs. As an alternative to conventional auto-injectors, many conventional drug delivery systems are designed to be wearable and to deliver a drug more slowly to the patient. While these conventional wearable drug delivery devices provide advantages, they can also suffer from certain problems in operation.

One problem with conventional wearable drug delivery devices is that, under certain circumstances, fluid from the user's body can undesirably be forced back into the fluid path of the drug delivery device. As will be appreciated, during drug delivery using a wearable device, the device and the user's body can be part of a balanced pressure system. Thus, if the pressure in the system is disturbed, undesirable backflow can occur. This, in turn, can cause clogging of the fluid path and/or can result in incorrect dosage to the patient. The problem can be particularly acute when the backflow includes blood, which can coagulate in the fluid delivery path causing the aforementioned clogging, and which, as mentioned, can prevent delivery of the drug and/or incorrect dosage to the patient.

Another problem with conventional wearable drug delivery devices is that, during filling with a liquid drug, there exists the possibility that air bubbles can become trapped in the liquid drug if the user does not properly purge the air. Priming techniques may thus be employed to remove trapped air and also to fill parts of the fluid path with deliverable liquid drug. Trapped air in the fluid path can present problems because air is compressible and can create compliance within a hydraulic drug delivery system. Compliance in the system and compressibility of air due to pressure or temperature can undesirably allow interstitial pressure to migrate bodily fluids, such as blood, into the fluid path and even into the associated liquid drug reservoir. If blood is allowed to migrate into the fluid path, it can coagulate and occlude the flow path, hindering the device's ability to deliver the liquid drug in a desired controlled manner.

In view of the above, it would be desirable to provide a drug delivery device that prevents undesirable backflow of fluids in the drug delivery path, eliminates air from the delivered liquid drug, and ensures uninterrupted delivery of liquid drug to the user.

DETAILED DESCRIPTION

This disclosure presents various systems, components, and methods for delivering a liquid drug or medicine to a patient or user. Each of the systems, components, and methods disclosed herein provides one or more advantages over conventional systems, components, and methods.

Various embodiments include a wearable drug delivery device that can deliver a liquid drug stored in a container to a patient or user. A soft needle or cannula can be placed in fluid communication with the liquid drug and can be coupled to a needle insertion component that provides access to the patient. A drive system of the drug delivery device can expel the liquid drug from the container to the patient through the soft needle or cannula. The result is enhanced comfort of the patient when using the drug delivery device. Correct dosage to the patient can also be assured. Any type of liquid drug can be stored by the drug delivery device and delivered to a patient. In various embodiments, the container can contain any therapeutic agent such as, for example, a drug, a subcutaneous injectable, a medicine, or a biologic. Other embodiments are disclosed and described.

Figure 1:
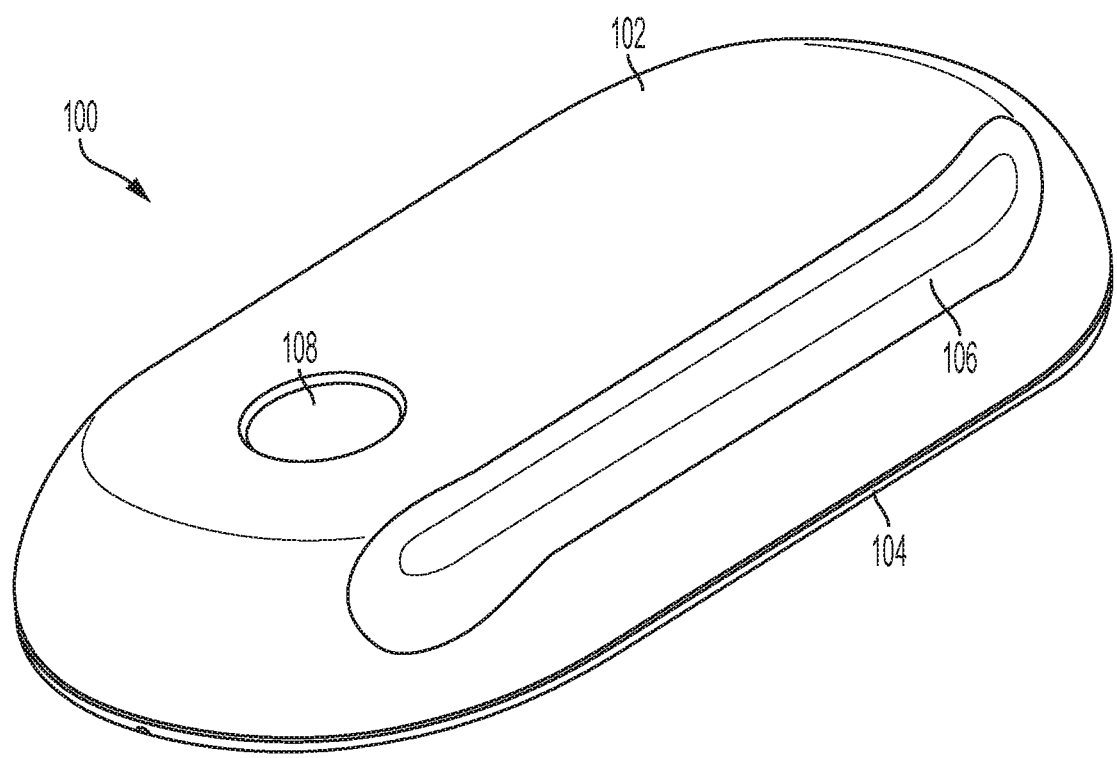
FIG. 1 illustrates an exemplary drug delivery device.

FIG. 1 illustrates an exemplary embodiment of a drug delivery device 100. The drug delivery device 100 can include a top portion or cover 102 and a lower portion or base 104. The top portion 102 and the lower portion 104 can together form a housing of the drug delivery device 100. The top portion 102 and the lower portion 104 can be coupled together to form an outside of the drug delivery device 100. The top portion 102 and the lower portion 104 can be formed from any material including, for example, plastic, metal, rubber, or any combination thereof.

The top portion 102 of the drug delivery device 100 can include a raised portion 106 that is elongated and runs along a side of the drug delivery device 100. A liquid drug cartridge (not shown) can be approximately positioned under the raised portion 106 such that the raised portion 106 accommodates the size and positioning of a liquid drug container within the drug delivery device 100. The top portion 102 can also include a patient interaction element or component 108. In various embodiments, the patient interaction element 108 can be a push button or other patient input device used to activate the drug delivery device 100.

The drug delivery device 100 can be a wearable drug delivery device 100. As a wearable device, the drug delivery device 100 can be part of an on-body delivery system (OBDS). The drug delivery device 100 can be coupled to a patient using an adhesive. The drug delivery device 100 can operate as a bolus drug delivery device, or as a continuous drug delivery device. In general, the drug delivery device 100 can provide any amount of a stored liquid drug to a patient over any period of time.

Figure 2:
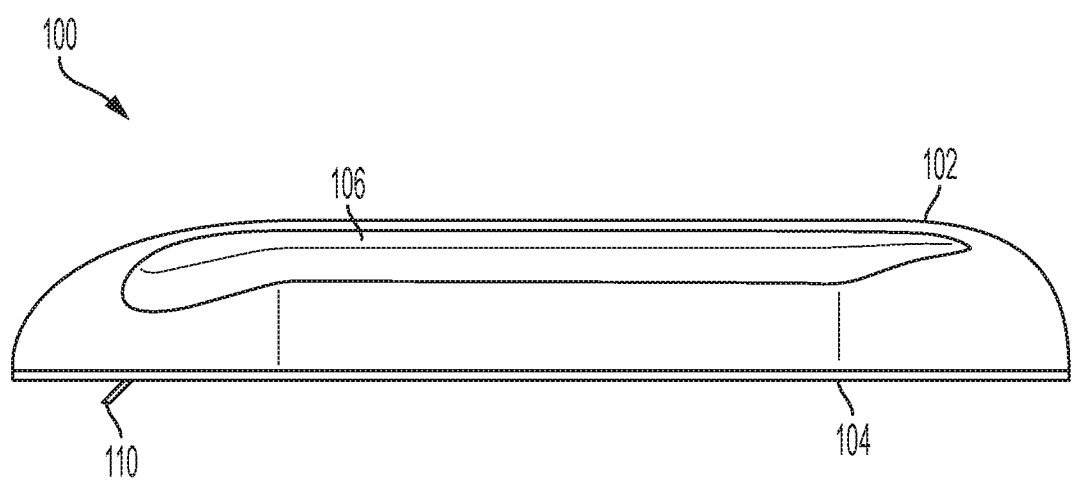
FIG. 2 illustrates a side view of the drug delivery device of FIG. 1.

FIG. 2 illustrates a side view of the drug delivery device 100. As shown, the drug delivery device 100 can include a soft needle or cannula 110 extending from the bottom portion 104 of the drug delivery device 100. The soft needle or cannula 110 can be a portion of a needle insertion mechanism. In some embodiments, the soft needle or cannula 110 extends from the drug delivery device 100 into the patient once a hard needle of the needle insertion mechanism has been retracted back inside the drug delivery device 100. The soft needle or cannula 110 can extend below the bottom portion 104 when attached to a patient and when delivering a liquid drug to the patient. In various embodiments, the soft needle or cannula 110 can remain extended outside of the drug delivery device 100 after activation.

Figure 3:
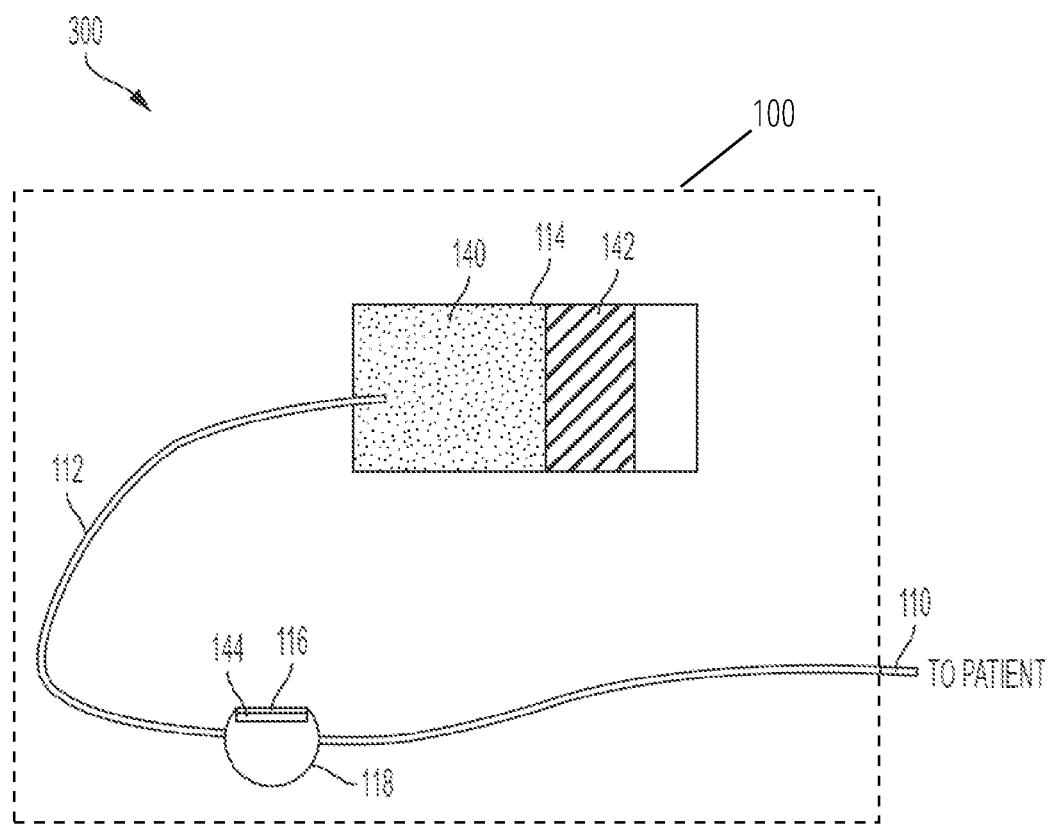
FIG. 3 illustrates an exemplary system for removing air from a fluid path of the drug delivery device of FIG. 1.

FIG. 3 illustrates a system 300 for removing air from a fluid path of the drug delivery device 100. The system 300 can include a fluid path 112 that employs air eliminating features. The system 300 can be a part or component of the drug delivery device 100. The fluid path 112 can couple a reservoir 114 to a patient or user of the drug delivery device 100. As an example, the fluid path 112 can provide fluid communication between the reservoir 114 and the soft needle or cannula 110 used to provide access to the body of the user of the drug delivery device 100. In various embodiments, the reservoir 114 can be a pre-filled cartridge.

The reservoir 114 can store or hold any type of liquid drug 140. As an example, the liquid drug 140 can be insulin. A plunger 142 can be positioned within the reservoir 114. The plunger 142 can be moved to expel the liquid drug 140 from the reservoir 114—by forcing the liquid drug 140 out of the reservoir 114, through the fluid path 112, and on to the soft needle or cannula 110 for delivery to the user. The fluid path 114 can be formed of a variety materials including, for example, plastic, metal, rubber, or any combination thereof. The plunger 142 can be considered to be a pump or pumping system, or a portion thereof, for extracting the liquid drug 140 from the reservoir 114.

It will be appreciated that for purposes of discussion, the term "fluid path" (or fluid path component) may be any portion of a fluid path within, or outside, the drug delivery device 100, which is employed to deliver the liquid drug 140 to a user. In the illustrated embodiment, the fluid path 112 runs from the reservoir 114 within the drug delivery device 100 to the soft needle or cannula 110, which can be located either inside or outside the drug delivery device 100.

As mentioned, the liquid drug 140 within the reservoir 114 and/or fluid path 112 can contain undesirable quantities of air. With conventional devices, such air may be eliminated from a fluid path using a separate priming step. During priming, a quantity of liquid drug from a liquid drug reservoir is ejected from the end of the drug delivery path to eliminate any air bubbles present in the fluid path. Such priming may not be effective, however, at eliminating air bubbles that exist far back in the fluid path (e.g., closer to the reservoir) or within the fluid reservoir. Thus, priming can be ineffective in ensuring that all air bubbles are removed from the reservoir and fluid path.

As shown in FIG. 3, the fluid path 112 can include a venting station or component 118. The venting station 118 can include an opening 144 in a wall of the fluid path 112. The opening can be blocked or covered by a membrane 116. The membrane 116 can comprise a liquid-proof and air-permeable (e.g., hydrophobic) material. The membrane 116 can prevent the liquid drug 140 from passing therethrough, while allowing any air bubbles entrained in the liquid drug 140 to pass therethrough. Specifically, any air or air bubbles within the liquid drug 140 can pass through the membrane 116 as the liquid drug 140 traverses the venting station 118 of the fluid path 112. In doing so, however, the liquid drug 140 is blocked from exiting the fluid path 112 and can be passed along to the soft needle or cannula 110.

In various embodiments, based on the arrangement of the venting station 118 and the fluid path 112 as shown in FIG. 3, when an air bubble enters the venting station 118, the pressure inherent in the system 300 will push the air out through the membrane 116 (while retaining the fluid therein), thus removing air bubbles from the liquid drug 140 in the fluid path 112.

It will be appreciated that the venting station 118 may be implemented at one or more locations along the length of the fluid path 112. In some embodiments, a venting station 118 can be implemented directly adjacent to, or as part of, the reservoir 114 itself.

In some embodiments, the discrete venting station 118 can be eliminated, and the membrane 116 can be directly attached to the fluid path 112 at one or more locations along the length thereof. As an example, the membrane 116 can form a portion of the fluid path 112 (such as a portion of a wall of the fluid path 112). Alternatively, in lieu of the membrane 116, relatively very small channels could be employed in the fluid path 112 itself. The channels can be sized so that they do not allow the liquid drug 140 to flow through (e.g., due to surface tension), but allow air to flow through.

It will be appreciated that with the system 300 and arrangements described in relation thereto, air elimination is automatically performed by the system 300, thereby eliminating the additional priming step which is required to be performed by a user of a conventional device.

Figure 4A:
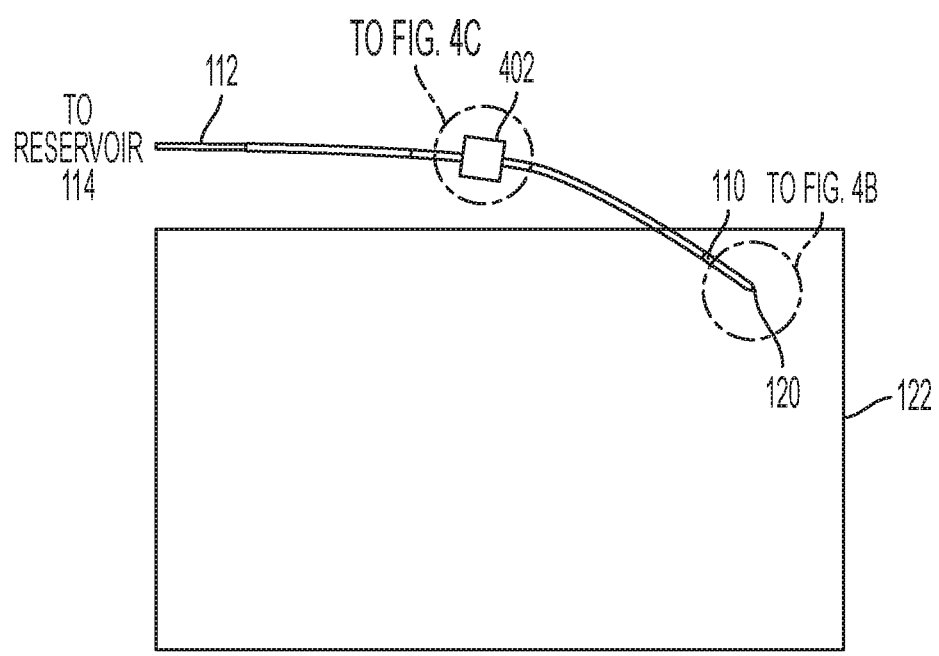
FIG. 4A illustrates a soft needle or cannula of the fluid path of the drug delivery device of FIG. 1 engaged with a user.
Figure 4B:
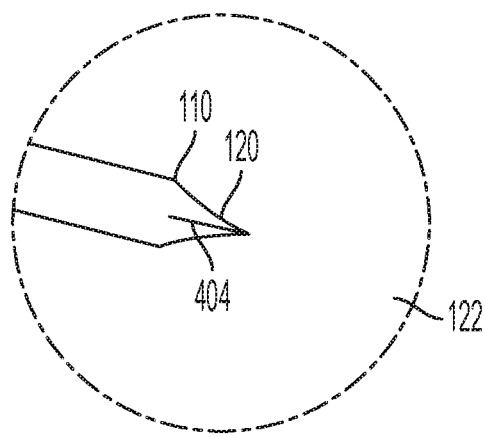
FIG. 4B illustrates a tip portion of the soft needle or cannula of FIG. 4A engaged with tissue of a user.
Figure 4C:
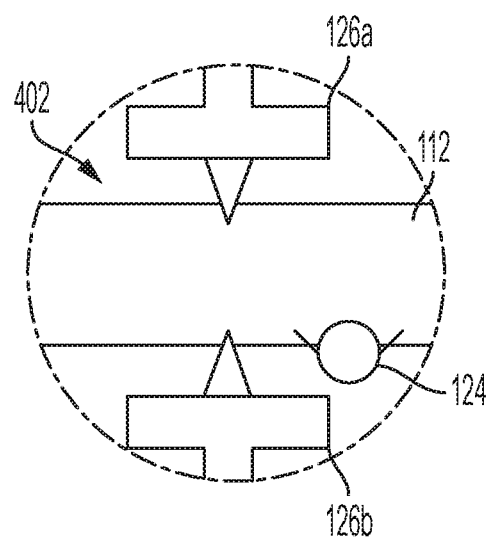
FIG. 4C illustrates a flow sensor system coupled to the fluid path of the drug delivery device of FIG. 1.

FIGS. 4A-4C illustrate arrangements for preventing fluid from flowing back into the fluid path 112. As mentioned, conventional drug delivery devices can, under certain circumstances, allow fluid from the user's body to flow back into a fluid path of a drug delivery device. Backflow can cause undesirable clogging of the fluid path and/or can result in incorrect dosage of liquid drug to the patient. FIG. 4A illustrates the soft needle or cannula 110 of the fluid path 112 engaged with a user. FIG. 4B illustrates a tip portion 120 of the soft needle or cannula 110 engaged with tissue 122 of the user. FIG. 4C illustrates a flow sensor system 402 coupled to the fluid path 112.

As shown in FIG. 4A, the fluid path 112 is shown coupling the reservoir 114 to the tip portion 120 of the soft needle or cannula 110. The tip portion 120 can be engaged with the tissue 122 of a user. The soft needle or cannula 110 can be part of the fluid path 112, which itself is fluidically coupled to the reservoir 114 containing the liquid drug 140 (not shown in FIG. 4A for simplicity).

FIG. 4B shows a close-up view of the tip portion 120 of the soft needle or cannula 110 engaged with the tissue 122 of the user. As shown in FIG. 4B, the tip portion 120 of the soft needle or cannula 110 can have a "duckbill" feature 404 attached to, or otherwise integrated into, the soft needle or cannula 110. The duckbill feature 404 can comprise an opening or slit at approximately a center of the tip portion 120 that can open or close. The duckbill feature 404 can be a one-way valve that can only open with a positive pressure imposed from inside the drug delivery device 100, which in some embodiments can be created by the plunger 142 used to dispense the liquid drug 140. In the event that pressure in the user's body (i.e., tissue pressure) is greater than the pressure in the fluid path 112, the duckbill feature 404 can seal itself (as shown in FIG. 4B) and will not allow fluid to travel back into the fluid path 112.

Alternatives to the duckbill feature 404 can include the use of one or more one-way check valves (e.g., ball valves) and/or alternative tip arrangements that enable flow in one direction but prevent flow in an opposite direction (e.g., allow flow from the fluid path 112 to the tissue 122 of the user but prevent flow from the user into the fluid path 112).

FIG. 4A illustrates the flow sensor system 402 coupled to the fluid path 112. In various embodiments, one or more flow sensor systems can be coupled to the fluid path 112. FIG. 4C shows a close-up view of the flow sensor system 402. The flow sensor system 402 can include a flow sensor 124 positioned to detect the direction of fluid flow through the fluid path 112. If the flow sensor 124 senses that fluid is moving backwards (i.e., from the user to the reservoir 114), then the flow sensor system 402 can activate a "pinch point" to prevent fluid from flowing through the fluid path 112. As shown in FIG. 4C, the pinch point can include a pair of opposing clamping elements 126a and 126b (e.g., as part of the flow sensor system 402), which are positioned on opposite sides of the fluid path 112. In various embodiments, the opposing clamping elements 126a and 126b can be positioned on opposite sides of the soft needle or cannula 110.

The flow sensor system 402 (e.g., via a processor, a controller, or other logic) can, upon receiving signals from the flow sensor 124 indicative of flow moving backwards through the fluid path 112, cause the clamping elements 126a, 126b to move toward each other sufficiently to constrict the fluid path 112, thus preventing flow through the fluid path 112. It will be appreciated that in some embodiments, a mechanical fluid flow detector could be employed in lieu of the flow sensor 124. A mechanical fluid flow detector may be desirable for fully-mechanical implementations of the drug delivery devices 100.

Figure 5:
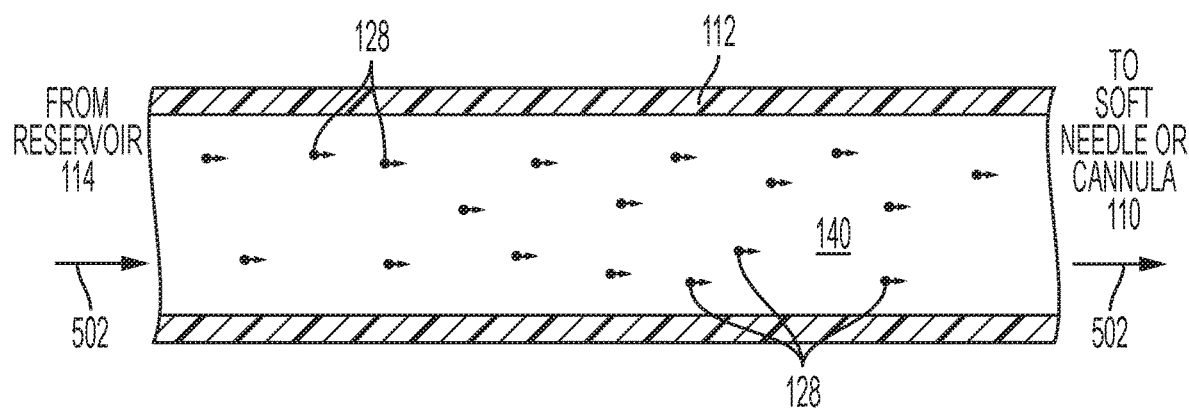
FIG. 5 illustrates a technique for preventing coagulation of fluid within the fluid path of the drug delivery device of FIG. 1.

FIG. 5 illustrates an arrangement and/or a technique for preventing coagulation within the fluid path 112 of the drug delivery device 100. As mentioned, coagulation-based clogging of a fluid path can occur when blood flows from a tissue site, back through the fluid path. If the blood is quickly expelled out through the fluid path, coagulation is not an issue. If blood is allowed to remain in the fluid path, however, coagulation can become a problem.

The disclosed arrangement and/or technique can include applying a slow, steady fluid flow (as indicated by flow arrows 502) through the fluid path 112 and out of the soft needle or cannula 110, thus ensuring that blood will not remain in the fluid path 112 long enough to coagulate and block the fluid path.

In such embodiments, a minimum flow rate of about 0.25 microliters per hour of liquid through the fluid path 112 may be employed to ensure that entrained particles 128 are always moving toward the delivery site (i.e., from the reservoir 114 toward the user) and thus cannot coagulate. This flow rate can be controlled either mechanically or electronically, via the pumping arrangement of the drug delivery device 100. This minimum flow rate can be provided by a pumping mechanism (e.g., a plunger) configured to extract a fluid from the reservoir 114.

While certain embodiments of the present invention have been described, it is expressly noted that the present invention is not limited to those embodiments. Rather, the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A wearable drug delivery device, comprising:
a top portion and a bottom portion;
a reservoir between the top portion and the bottom portion and configured to store a liquid drug;
a needle insertion component operable to extend a cannula from the bottom portion into a user, and
a fluid path component between the top portion and the bottom portion coupling the reservoir to the cannula, the fluid path component configured to enable delivery of the liquid drug to the user of the drug delivery device when the liquid drug is expelled from the reservoir, wherein the fluid path component includes:
a venting component, the venting component configured to retain the liquid drug while allowing air within the liquid drug to pass through the venting component and out of the fluid path component.

2. The wearable drug delivery device of claim 1, the venting component comprising an opening within the fluid path component and a membrane covering the opening.

3. The wearable drug delivery device of claim 2, the membrane comprising a liquid-proof and air-permeable material.

4. The wearable drug delivery device of claim 3, the fluid path component comprising an additional venting component positioned directly adjacent to the reservoir.

5. The wearable drug delivery device of claim 3, the fluid path component further includes a flow sensor system.

6. The wearable drug delivery device of claim 5, the flow sensor system comprising a flow sensor, a first clamping component, and a second clamping component.

7. The wearable drug delivery device of claim 6, the flow sensor configured to detect a direction of a flow of the liquid drug in the fluid path component.

8. The wearable drug delivery device of claim 7, the first and second clamping components positioned on opposite sides of the fluid path component.

9. The wearable drug delivery device of claim 8, the first and second clamping components configured to move toward each other to constrict the fluid path component to prevent the flow of the liquid drug in the fluid path component.

10. The drug wearable delivery device of claim 9, the first and second clamping components configured to constrict the fluid path component to prevent the flow of the liquid drug when the flow sensor detects the direction of the flow is from the user toward the reservoir.

11. The wearable drug delivery device of claim 9, the first and second clamping components configured to not constrict the fluid path component to prevent the flow of the liquid drug when the flow sensor detects the direction of the flow is from the reservoir to the user.

12. The drug wearable delivery device of claim 6, the first and second clamping components positioned on opposite sides of the cannula.

13. The wearable drug delivery device of claim 1, the cannula comprising a tip portion having a duckbill feature, the duckbill feature comprising a slit positioned at approximately a center of the tip portion.

14. The wearable drug delivery device of claim 1, the cannula comprising a tip portion having a one-way check valve configured to enable flow of the liquid drug out of the tip portion to the user while preventing flow into the tip portion.

15. The wearable drug delivery device of claim 1, further comprising a pumping system configured to maintain a minimum flow rate of the liquid drug of 0.25 microliters per hour through the fluid path component.

16. The wearable drug delivery device of claim 15, the pumping system comprising a plunger positioned within the reservoir.

17. The wearable drug delivery device of claim 1, wherein the reservoir comprises a pre-filled cartridge.

18. The wearable drug delivery device of claim 17, wherein the liquid drug is insulin.

19. The wearable drug delivery device of claim 1, further comprising:
   an adhesive to secure the wearable drug delivery device to the user.

20. The wearable drug delivery device of claim 19, wherein:
   the adhesive is disposed on the bottom portion of the wearable drug delivery device facing the user.

\* \* \* \* \*